(12) United States Patent
Pei et al.

(10) Patent No.: US 11,827,901 B2
(45) Date of Patent: Nov. 28, 2023

(54) **USE OF *CISTANCHE DESERTICOLA* POLYSACCHARIDES IN PROMOTING PROLIFERATION AND DIFFERENTIATION OF FEMALE GERMLINE STEM CELLS**

(71) Applicant: Ningxia Medical University, Yinchuan (CN)

(72) Inventors: Xiuying Pei, Yinchuan (CN); Xiaoli Yu, Yinchuan (CN); Yikai Qiu, Yinchuan (CN); Ji Wu, Yinchuan (CN); Jianqiang Yu, Yinchuan (CN); Yanrong Wang, Yinchuan (CN); Xinrui Liu, Yinchuan (CN); Jing Pu, Yinchuan (CN)

(73) Assignee: Ningxia Medical University, Yinchuan (CN)

( * ) Notice: Subject to any disclaimer, the term of this patent is extended or adjusted under 35 U.S.C. 154(b) by 142 days.

(21) Appl. No.: 17/211,866

(22) Filed: Mar. 25, 2021

(65) Prior Publication Data
US 2021/0371814 A1 Dec. 2, 2021

(30) Foreign Application Priority Data
May 28, 2020 (CN) .......................... 202010467245.0

(51) Int. Cl.
*C12N 5/075* (2010.01)

(52) U.S. Cl.
CPC ........ *C12N 5/0609* (2013.01); *C12N 2500/32* (2013.01); *C12N 2501/11* (2013.01); *C12N 2501/115* (2013.01); *C12N 2501/13* (2013.01); *C12N 2501/235* (2013.01); *C12N 2501/90* (2013.01); *C12N 2506/04* (2013.01)

(58) Field of Classification Search
CPC combination set(s) only.
See application file for complete search history.

(56) References Cited

PUBLICATIONS

Cooper, Geoffrey M. "The Cell: A Molecular Approach. Sunderland (MA) Sinauer Associates." Structure and Organization of Actin Filaments. (Year: 2000).*

Dong, Qun, et al. "Structural characterization and immunological activity of two cold-water extractable polysaccharides from Cistanche deserticola YC Ma." Carbohydrate Research 342.10: 1343-1349. (Year: 2007).*

Zhang, Jing-Ping, et al. "Down-regulation of Sp1 suppresses cell proliferation, clonogenicity and the expressions of stem cell markers in nasopharyngeal carcinoma." Journal of translational medicine 12.1:1-12. (Year: 2014).*

Zhang, Ying, et al. "The difference of chemical components and biological activities of the raw products slices and the wine steam-processed product from Cistanche deserticola." Evidence-Based Complementary And Alternative Medicine. (Year: 2019).*

Li, Wen-lan, et al. ("Screening of phytoestrogenic effective extracts and dose of Cistanche deserticola." Chinese Herbal Medicines 5.4: 292-296 (Year: 2013).*

* cited by examiner

*Primary Examiner* — Marcia S Noble
*Assistant Examiner* — Josephine M Gonzales
(74) *Attorney, Agent, or Firm* — Bayramoglu Law Offices LLC

(57) ABSTRACT

Use of *Cistanche deserticola* polysaccharide (CDP) in promoting the proliferation and differentiation of female germline stem cells (FGSCs) is provided. Specifically, the addition of CDP in an in vitro cultivation system can promote the proliferation and differentiation of FGSCs, and especially can enhance the in vitro directed differentiation of FGSCs into oocytes, which provides a new research reference for studying the generation of oocytes in vivo and in vitro and also brings a new hope for research on physiological infertility.

6 Claims, 12 Drawing Sheets

USE OF *CISTANCHE DESERTICOLA* POLYSACCHARIDES IN PROMOTING PROLIFERATION AND DIFFERENTIATION OF FEMALE GERMLINE STEM CELLS

CROSS REFERENCE TO THE RELATED APPLICATIONS

This application is based upon and claims priority to Chinese Patent Application No. 202010467245.0, filed on May 28, 2020, the entire contents of which are incorporated herein by reference.

TECHNICAL FIELD

The present invention belongs to the field of biotechnology, and specifically relates to the use of *Cistanche deserticola* polysaccharides (CDPs) in promoting the proliferation and differentiation of female germline stem cells (FGSCs).

BACKGROUND

FGSCs, also known as ovarian germline stem cells (OGSCs), are derived from primary germ cells (PGCs). They have the ability to differentiate into oocytes under induction, and are expected to replenish the constantly-depleted primordial follicle pool, which is a revolutionary discovery in reproductive biology. Traditionally, it is believed that the number of eggs in the ovaries of born mammals will not increase. A fixed number of eggs will be matured and released during the whole life of a female. With the depletion of follicles and the atrophy of an ovary, a female gradually enters into a menopause period from a childbearing period and thus loses fertility.

Studies have shown that newborn mice and adult mice have FGSCs that can regenerate eggs, and the presence of FGSCs in females at a childbearing period or menopause period and patients with premature ovarian failure (POF) has also been verified. FGSCs, derived from ovarian tissues, are germ cells that express germline markers, can undergo mitosis, and have the ability to proliferate. Achieving the proliferation and differentiation of FGSCs through stable in vitro cultivation has a profound impact for the basic research on the occurrence and development of germ cells and for the clinically treating infertility. There is no prior publication or disclosure, however, regarding use of CDPs in promoting the proliferation and differentiation of FGSCs.

SUMMARY

In view of the above-mentioned problems in the prior art, the present invention provides use of CDPs in promoting the proliferation and differentiation of FGSCs. CDPs can promote the proliferation and differentiation of FGSCs, and in particular can improve the ability of FGSCs to differentiate directly into oocytes in vitro.

To achieve the above objective, the present invention adopts the following technical solutions to solve the technical problems thereof.

Use of CDPs in promoting the proliferation and differentiation of FGSCs, specifically including adding CDPs in an in vitro cultivation system to promote the proliferation and differentiation of FGSCs, and in particular to enhance the in vitro directed differentiation of FGSCs into oocytes.

The above-mentioned cultivation system may be a conventional FGSC cultivation system, and the cultivation system includes: α-minimum essential medium (α-MEM)+1 mM non-essential amino acids (NEAAs)+2 mM L-glutamine+1 mM sodium pyruvate+0.1 mM β-mercaptoethanol (β-ME)+10 ng/ml leukemia inhibitory factor (LIF)+10 ng/ml epidermal growth factor (EGF)+40 ng/ml glial cell line-derived neurotrophic factor (GDNF)+1 ng/ml basic fibroblast growth factor (bFGF)+10% foetal bovine serum (FBS)+15 mg/ml penicillin/streptomycin.

When CDPs is added to the above-mentioned cultivation system at an amount of 0.25 μg/ml to 0.75 μg/ml, FGSCs are promoted in the proliferation and differentiation after being cultivated for 12 h to 48 h. In particular, when the added CDPs has a concentration of 0.5 μg/ml, the FGSCs have significantly-increased pluripotency and germline marker genes after being cultivated for 24 h and show significant induced differentiation after being cultivated for 48 h.

The use of CDPs in promoting the proliferation and differentiation of FGSCs provided in the present invention has the following advantages:

CDPs are one kind of the main active ingredients in a *Cistanche deserticola* plant, which is a polysaccharide compound formed from the polycondensation of monosaccharides such as glucose, galactose, rhamnose, and arabinose. CDPs can promote the proliferation and differentiation of FGSCs in vitro, that is, the addition of CDPs in an in vitro cultivation system can promote the proliferation and differentiation of FGSCs, and especially can enhance the in vitro directed differentiation of FGSCs into oocytes.

In the present invention, by sequencing the transcriptome of FGSCs treated with CDPs, it can be known that the signaling pathways related to cell proliferation and differentiation have changed, and the functions of genes related to stem cell growth and development show significant difference. Moreover, in the function of stem cell proliferation and differentiation, the down-regulation of key genes shows a reduced self-renewal ability and an enhanced differentiation ability of cells. It provides a new research reference for studying the generation of oocytes in vivo and in vitro and also brings a new hope for research on physiological infertility.

DETAILED DESCRIPTION OF THE EMBODIMENTS

Example 1

Figure 1A:
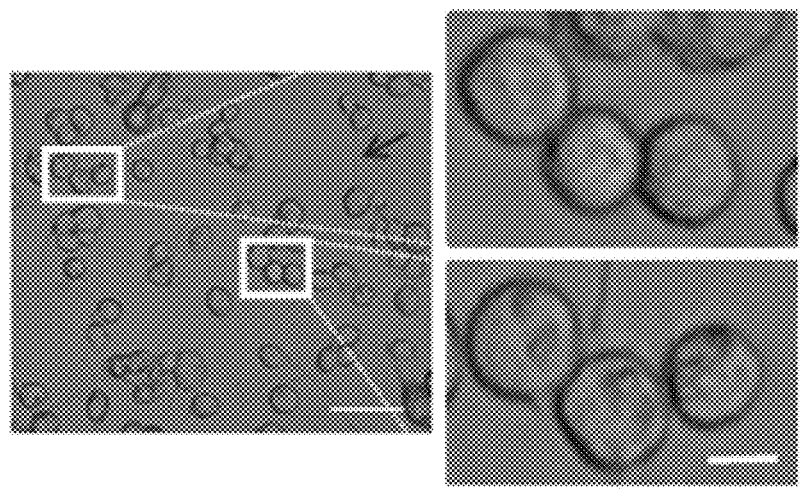
FIG. 1A is a diagram showing a state of mouse FGSCs (mFGSCs) cultivated in vitro.

1. Isolation of mFGSCs
   (1) A clean bench is subjected to ultraviolet (UV) disinfection before separating the cells, then 3 to 5 days-old female mice are sacrificed by cervical dislocation and put on the clean bench, and the abdomen of the mice is disinfected with 75% alcohol cotton balls. The abdomen of the mice is dissected as soon as possible to take out bilateral ovaries, the collected ovaries are put in a glass dish with 500 ul of D-Hanks, and then the dish is placed on ice for ice bath.
   (2) The ovaries are washed once with D-Hanks, then transferred to another dish with phosphate buffer saline (PBS), and chopped with scissors, thus facilitating enzyme digestion in the next step.

A resulting tissue suspension is pipetted to a centrifuge tube with a pipette, the 35 mm dish is rinsed with collagenase D-Hanks and a rinse is transferred to the centrifuge tube, and collagenase D-Hanks is supplemented.
   (3) The 15 ml centrifuge tube is placed in a 37° C. water bath and slowly shaken for 20 min of digestion until the tissue is dispersed, then the suspension is centrifuged at 1,000 rpm for 5 min, and a resulting supernatant is discarded. PBS is added to the centrifuge tube, a resulting solution is centrifuged at 1,000 rpm for 5 min, and a resulting supernatant is discarded.
   (4) 0.05% trypsin-containing D-Hanks is added, a resulting mixture is slowly shaken at 37° C. for 5 min of digestion (until the tissue is dispersed), and then FBS is added to terminate the digestion. Flocculent tissue blocks are carefully removed after digestion, a resulting solution is centrifuged at 1,000 rpm for 5 min, and a resulting supernatant is discarded as much as possible, ensuring that a resulting precipitate is not removed.
   (5) The cells are resuspended with a fresh FGSC culture solution, then added to a well plate covered with a feeder layer, and cultivated in a 37° C. incubator.

The FGSC culture solution includes the following components: α-MEM medium+1 mM NEAAs (GIBCO)+2 mM L-glutamine+1 mM sodium pyruvate+0.1 mM β-ME+10 ng/ml LIF+10 ng/ml EGF+40 ng/ml GDNF+1 ng/ml bFGF+10% FBS+15 mg/ml penicillin/streptomycin.

2. Purification of mFGSCs

The isolated mFGSCs are purified by magnetic-activated cell sorting (MACS), specifically including the following steps:
   (1) The mFGSCs isolated above are centrifuged at 1,000 rpm for 5 min, a resulting supernatant is discarded, and the cells are resuspended with D-Hanks; 200 µl of D-Hanks and 4 µl of MVH (0.5 µg/µl) primary antibody are thoroughly mixed in a new sterile centrifuge tube, and a resulting mixture is thoroughly mixed with the cell suspension; and a resulting mixture is incubated in a shaking incubator at 300 rpm and 37° C. for 30 min.
   (2) A mixture obtained from step (1) is centrifuged at 1,000 rpm for 5 min, and a resulting supernatant is removed; cells are washed once with D-Hanks, a resulting cell suspension is centrifuged at 1,000 rpm for 5 min, and a resulting supernatant is removed; 2 µl of secondary-antibody magnetic beads are added, and a resulting mixture is incubated at room temperature for 30 min, during which period, the tube is gently shaken once every 5 min to allow the full binding of the secondary-antibody magnetic beads with the primary antibody.
   (3) The centrifuge tube is left at room temperature for 2 min on an MACS rack, and then all the liquid is gently removed; 200 µl of D-Hanks is added to the centrifuge tube, then the tube is left at room temperature for 2 min once again on the MACS rack, and then all the liquid is removed so that all cells unbind to the magnetic beads are removed.
   (4) The cells are resuspended with a fresh FGSC culture solution, then added to a well plate covered with a feeder layer, and cultivated in a 37° C. incubator; and after a few days of cultivation, the magnetic beads fall off automatically, and purified cells are obtained through subcultivation.

3. Subcultivation of mFGSCs
   (1) The culture solution in the culture plate is pipetted away with a pipette, pre-heated PBS is added to the culture plate for washing the cells, and then the PBS is pipetted away; 0.05% trypsin is added to the culture plate, and a resulting mixture is incubated for 1.5 min in a 37° C. incubator or on a clean bench; and an equal volume of culture solution is added to the petri dish to terminate the digestion of trypsin.
   (2) A resulting solution is slowly pipetted up and down with a pipette to make all cells fall off from the bottom of the culture plate, and a resulting mixture is transferred to a centrifuge tube and centrifuged at 1,000 rpm for 5 min; a resulting supernatant is pipetted away with a pipette and a fresh FGSC culture solution is added to the tube; and the culture solution is pipetted up and down to make the cell cluster at the bottom of the tube resuspended.
   (3) A resulting cell suspension is added by a pipette to a 48-well plate covered with an STO cell feeder layer, which is slowly pipetted up and down to make the cells evenly distributed; and then the plate is slowly transferred in a 37° C. incubator for cultivation.

Figure 1B:
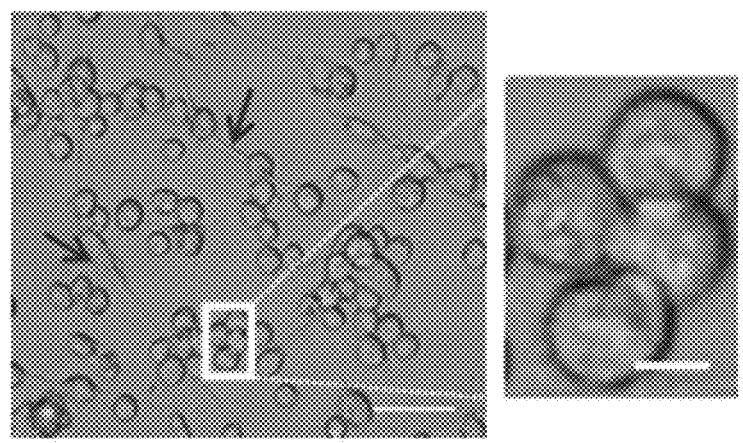
FIG. 1B is a diagram showing the state of mFGSCs cultivated in vitro from another view.

A state of mFGSCs cultivated in vitro is shown in FIGS. 1A-B. FIG. 1A and FIG. 1B are both images magnified 400 times, with scale lengths of 50 μm and 10 μm, respectively.

4. EdU Proliferation Activity Assay of mFGSCs (1) FGSCs with appropriate growth state and density are selected and spread in a 24-well plate with glass slides, and the cells are allowed to grow on the slides for 4 h; after cells are adhered to the slides, a medium is prepared and subsequent experimental steps are conducted according to an EdU test kit instruction manual to obtain immunofluorescence glass slides for FGSC proliferation assay.

Figure 2:
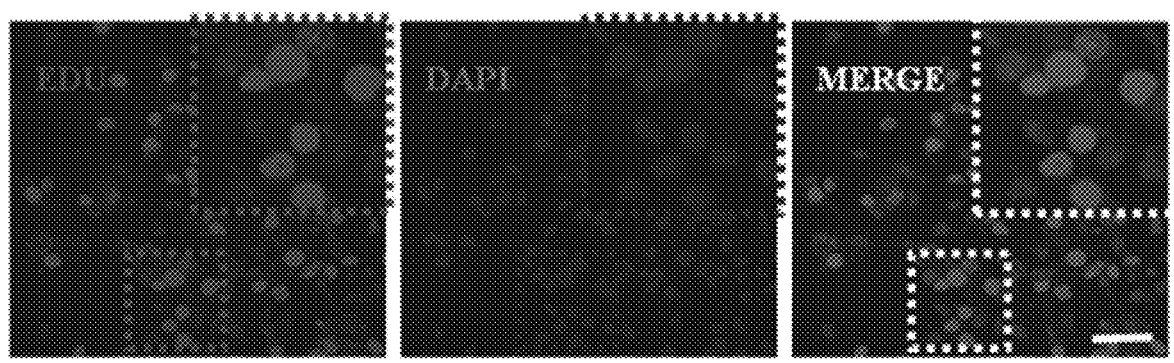
FIG. 2 is a diagram showing the detection results of the proliferation activity of mFGSCs in vitro.

(2) An anti-fluorescence quenching agent is dropped onto a concave glass slide, then the immunofluorescence glass slide is upended at the center of the concave glass slide, and the slides are mounted with a mountant and then placed under a fluorescence microscope for observing and taking pictures. Results are shown in FIG. 2, where, the images are magnified 400 times, with a scale length of 50 μm.

5. Identification of mFGSCs (1) RT-PCR and PCR detection of mFGSCs, including the following steps:

A. FGSCs with a growth density of about 80% are collected, RNA is extracted according to a micro RNA extraction kit instruction manual, and RNA samples meeting standards are assayed by a micro spectrophotometer and numbered for later use.

B. With a 2,000 ng/tube as a system, reverse transcription is conducted for the obtained RNA samples according to a reverse transcription kit instruction manual to obtain cDNA samples.

C. Based on instructions of a PCR kit, the germ stem cell marker gene Oct4 and germ cell marker genes Mvh/Fragilis/Dazl and stem cell marker genes Stella/Blimp1/Sycp3/Gapdh are detected.

The Touchdown PCR Procedure is Set as Follows:

| | | |
|---|---|---|
| 94° C. | 3 min | |
| 94° C. | 30 sec | |
| 64° C. | 30 sec | 2 cycles |
| 72° C. | 1 min | |
| 94° C. | 30 sec | |
| 62° C. | 30 sec | 2 cycles |
| 72° C. | 1 min | |
| 94° C. | 30 sec | |
| 60° C. | 30 sec | 2 cycles |
| 72° C. | 1 min | |
| 94° C. | 30 sec | |
| 58° C. | 30 sec | 2 cycles |
| 72° C. | 1 min | |
| 94° C. | 30 sec | |
| 56° C. | 30 sec | 2 cycles |
| 72° C. | 1 min | |
| 94° C. | 30 sec | |
| 54° C. | 30 sec | 2 cycles |
| 72° C. | 1 min | |
| 94° C. | 30 sec | |
| 52° C. | 30 sec | 2 cycles |
| 72° C. | 1 min | |
| 94° C. | 30 sec | |
| 50° C. | 30 sec | 20 cycles |
| 72° C. | 1 min | |
| 72° C. | 5 min | |
| 4° C. | forever | |

Figure 3:
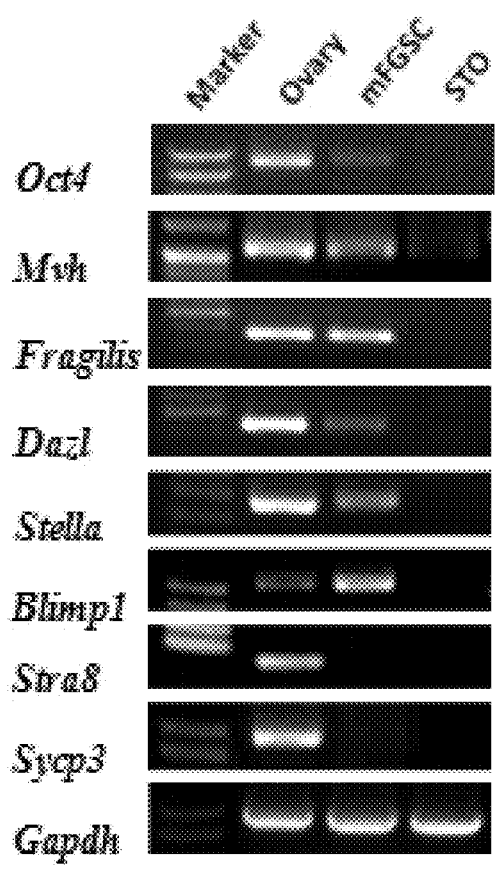
FIG. 3 is a diagram showing the result of agarose gel electrophoresis.

D. The PCR products are detected by 2% agarose gel electrophoresis. Results are shown in FIG. 3. FIG. 3 shows the expression of the germ cell germline genes Mvh(228 bp) Fragilis(264 bp) Dazl(328 bp), FGSC genes Oct4(430 bp) Stella(354 bp) Blimp1(483 bp) and differentiation genes Stra8(135 bp) Scp3(437 bp), and internal reference Gapdh. From left to right, the lanes indicate DNA marker, ovaries (positive control), FGSCs, and STO cells (negative control).

(2) IFA of FGSCs

A. In a 24-well plate, the FGSC-growing glass slides are immersed in PBS for 3 times, 5 min/time; and the slides are fixed with 4% paraformaldehyde (PFA) for 15 min and then immersed in PBS for 3 times, 5 min/time.

B. The cells are permeabilized with 0.5% Triton X-100 at room temperature for 10 min, then the Triton is removed, and the slides are immersed in PBS for 3 times, 5 min/time; blocking is conducted for 1 h with BSA at room temperature, without washing; then a rabbit primary antibody Oct4 (diluted at 1:400) and Mvh (diluted at 1:100) are added to the 24-well plate; and the plate is sealed with parafilm and incubated overnight at 4° C.

C. The slides are immersed in PBS for 3 times, 5 min/time, a goat anti-rabbit fluorescent secondary antibody (diluted at 1:400) is added in the dark, and the slides are incubated for 1 h in a humidified box at room temperature; and then the slides are immersed in PBS for 3 times, 5 min/time.

D. Counter-staining of nuclei: DAPI (diluted at 1:1,000) is added dropwise and the slides are incubated in the dark for 3 min (which is determined according to cell quality); excess DAPI is washed away by conducting PBS washing 2 times, 5 min/time; an anti-fluorescence quenching agent is dropped on a glass slide, the stained glass slide is upended on the glass slide, and then the slides are mounted; and observation and image acquisition are conducted under a fluorescence microscope. Results are shown in FIG. 4.

Figure 4:
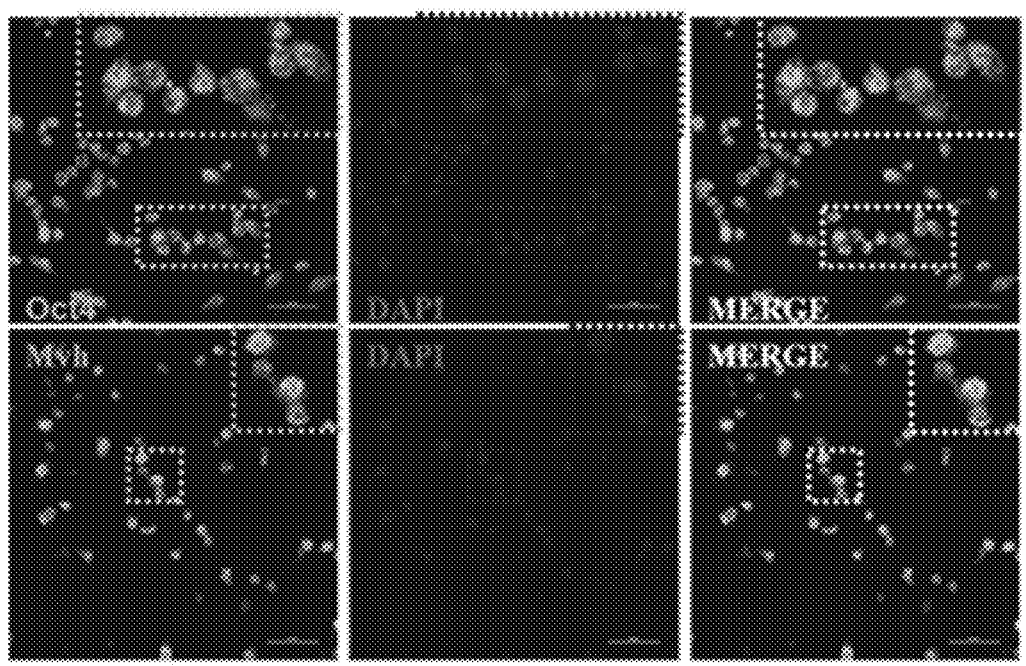
FIG. 4 is a diagram showing the immunofluorescence assay (IFA) result of FGSCs.

FIG. 4 shows the expression of Oct4 and Mvh in FGSCs, where, Oct4 and Mvh are green, and the images are magnified 400 times, with a scale length of 50 μm.

6. Treatment of FGSCs with CDPs (1) FGSCs at a well growth state and a density of about 80% to 90% are selected for subcultivation. After the cells are adherent one night later, CDPs culture solutions (purchased from Shanghai Yuanye Biotech Co., Ltd., analytical standard with a purity greater than 98%) at different concentrations (experimental groups) and a normal FGSC culture solution (control group) are added, separately. The CDPs at first screening concentrations are as follows: 50 g/ml, 5 μg/ml, and 0.5 μg/ml.

CDPs-containing culture solutions at the first screening concentrations are obtained by adding CDPs at an amount of 50 μg/ml (or 5 μg/ml or 0.5 μg/ml) to an FGSC culture solution.

(2) After the above experimental verification, it is determined that the lowest concentration of 0.5 μg/ml among the first screening concentrations exhibits the optimal effect. Therefore, on the basis of this concentration, the following CDPs at second screening concentrations with narrowed differences are selected for further verification: 0.75 μg/ml, 0.5 μg/ml, and 0.25 μg/ml.

CDPs-containing culture solutions at the second screening concentrations are obtained by adding CDPs at an amount of 0.75 μg/ml (or 5 μg/ml or 0.25 μg/ml) to an FGSC culture solution.

(3) Relevant experimental tests are conducted at 12 h, 24 h, 36 h, and 48 h of cultivation in CDPs-containing culture solutions, and then statistical analysis is conducted.

Figure 5A:
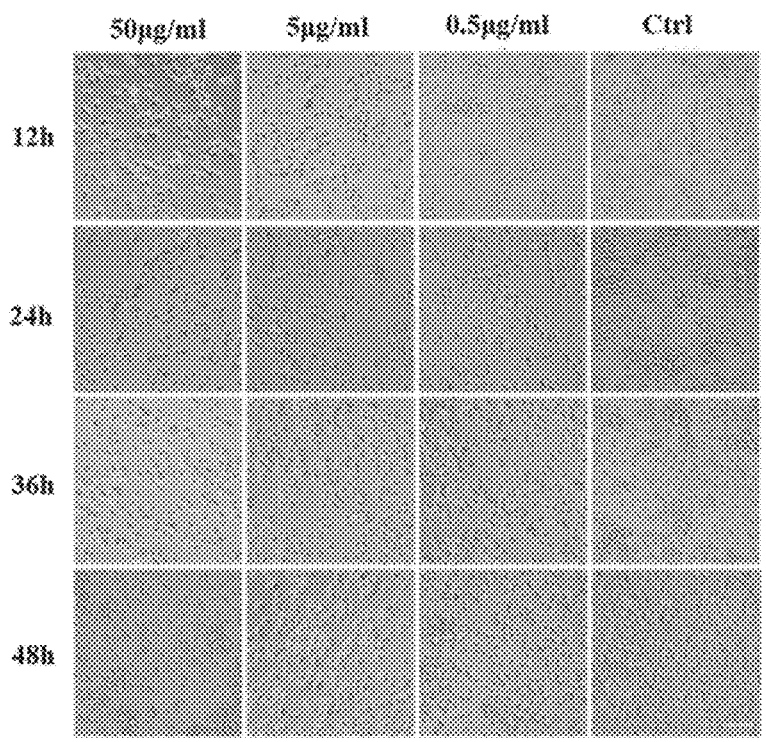
FIG. 5A is a diagram showing morphologies of mFGSCs treated in vitro with CDPs at first screening concentrations and at different time points.
Figure 5B:
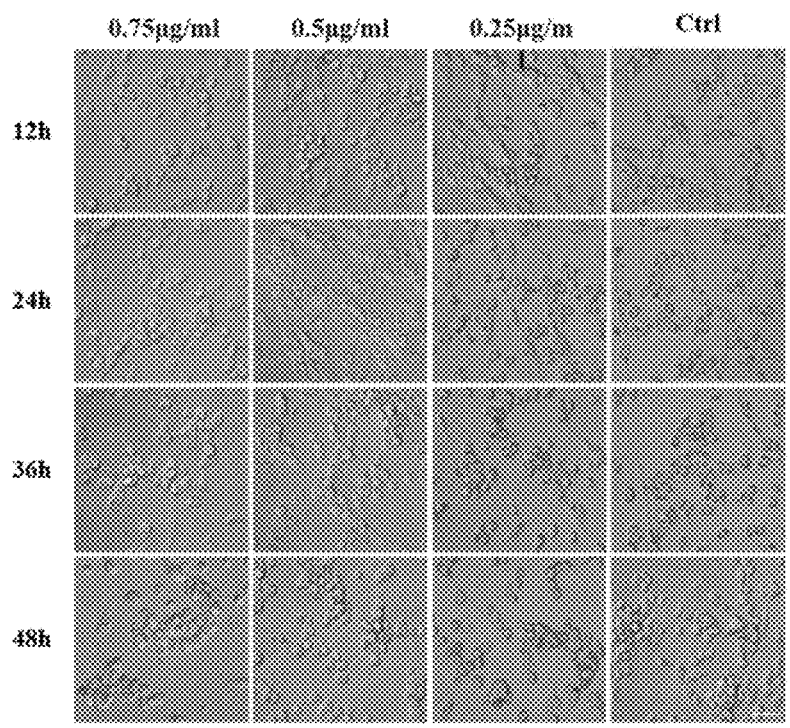
FIG. 5B is a diagram showing morphologies of mFGSCs treated in vitro with CDPs at second screening concentrations and at different time points.

The morphologies of mFGSCs treated in vitro with CDPs at different concentrations and at different time points are shown in FIGS. 5A-B, where, the images are magnified 100 times, with a scale length of 100 μm. FIG. 5A shows the morphologies of mFGSCs treated with the CDPs-containing culture solutions at first screening concentrations; and FIG. 5B shows the morphologies of mFGSCs treated with CDPs-containing culture solutions at second screening concentrations.

7. Detection of the Proliferation Activity of Treated FGSCs by CCK8
   (1) FGSCs at an appropriate growth state are spread in a 96-well plate, with 4 replicate wells for each group of cells, and the cells are cultivated overnight for adhesion. Then a test is conducted according to a CCK8 test kit instruction manual, and optical density (OD) values are determined at 12 h, 24 h, 36 h, and 48 h of CDPs treatment.
   (2) The Graphpad prism software is used for analysis and plotting based on the obtained data. Results are shown in FIGS. 6A-B.

Figure 6A:
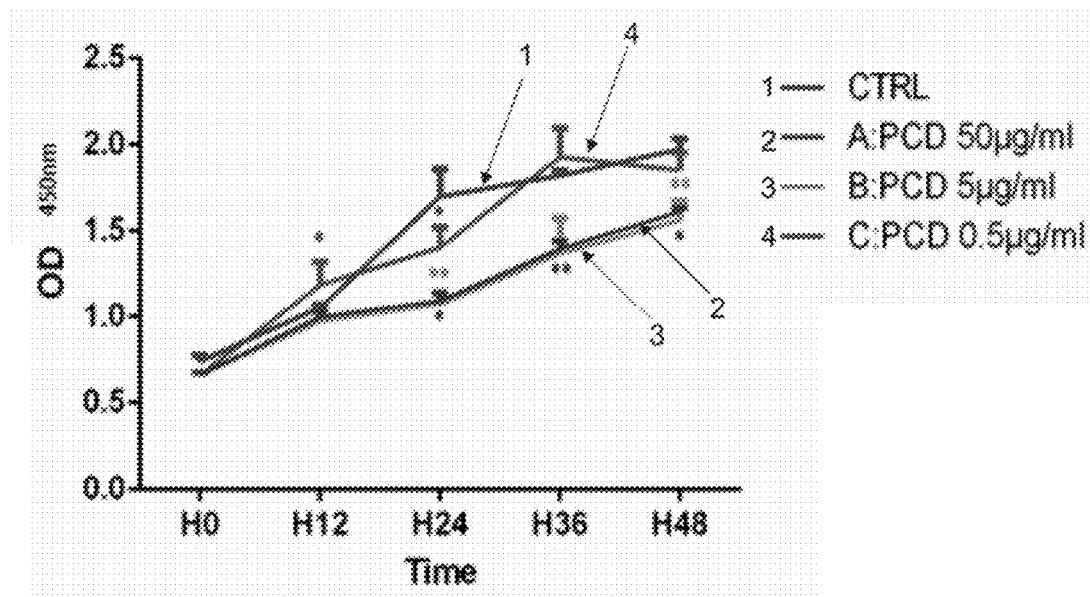
FIG. 6A is a diagram showing the detection results of the proliferation activity of FGSCs treated with CDPs, where, the group A has a CDPs concentration of 50 μg/ml, the group B has a CDPs concentration of 5 μg/ml, the group C has a CDPs concentration of 0.5 μg/ml.

FIG. 6A shows the results of the proliferation activity of FGSCs at 0 h, 12 h, 24 h, 36 h, and 48 h of CDPs treatment from high concentration A to low concentration C, where, the group A has a CDPs concentration of 50 μg/ml, the group B has a CDPs concentration of 5 μg/ml, the group C has a CDPs concentration of 0.5 μg/ml, and the Ctrl group refers to a control group. FIG. 6A shows that the group C has a cell viability close to that of the Ctrl group, and the groups A and B have a cell viability lower than that of the Ctrl group.

Figure 6B:
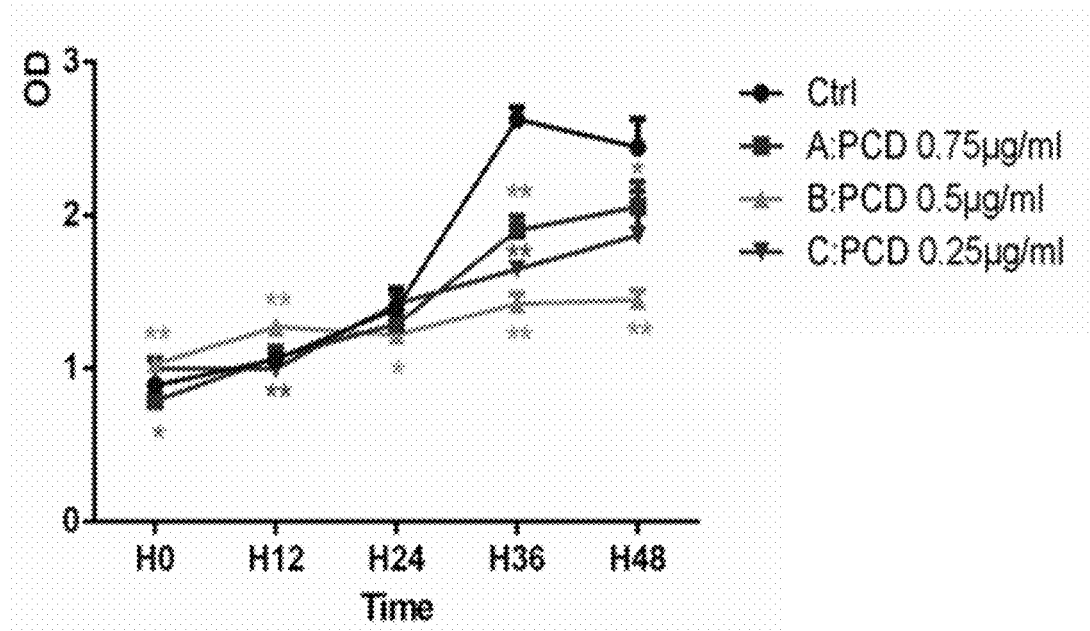
FIG. 6B is a diagram showing the detection results of the proliferation activity of FGSCs treated with CDPs, where, the group A has a CDPs concentration of 0.75 μg/ml, the group B has a CDPs concentration of 0.5 µg/ml, the group C has a CDPs concentration of 0.25 µg/ml.

In FIG. 6B, the group A has a CDPs concentration of 0.75 μg/ml, the group B has a CDPs concentration of 0.5 μg/ml, the group C has a CDPs concentration of 0.25 μg/ml, and the Ctrl group refers to a control group.

The data for A, B, and C refer to mean±standard deviation (SD) of three experiments, and the data are processed by analysis of variance (ANOVA). * indicates $P<0.05$ and ** indicates $P<0.01$.

8. Detection of the expression of related genes in treated FGSCs by quantitative fluorescence PCR (QF-PCR)
   (1) FGSCs treated with CDPs and normally-cultivated FGSCs are adopted as an experimental group and a control group, respectively. Cell samples are collected by digestion at 12 h, 24 h, 36 h, and 48 h of cultivation and numbered, RNA is extracted according to a micro RNA extraction kit instruction manual, and RNA samples meeting standards are assayed by a micro spectrophotometer and numbered for later use.
   (2) With a 200 ng/tube as a system, reverse transcription is conducted for the numbered RNA samples according to a reverse transcription kit instruction manual to obtain corresponding cDNA samples.
   (3) A test is conducted in accordance with a QF-PCR kit instruction manual to detect the expression of related genes in GSCs, and obtained data are imported into the Graphpad prism software for analysis and plotting. Results are shown in FIGS. 7A-B, where, each group of histograms includes group Ctrl, group A, group B, and group C from left to right.

Figure 7A:
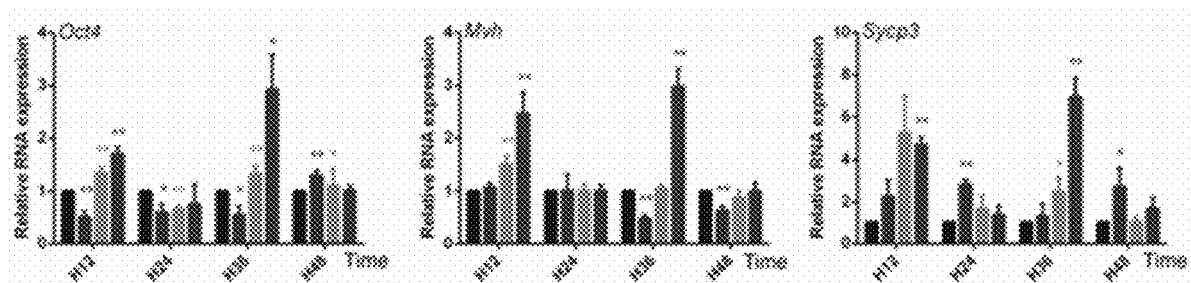
FIG. 7A is a diagram showing the expression of related genes Oct4(A) Ddx4(B) Sycp3(C) in FGSCs treated with CDPs.

FIG. 7A shows the relative expression of genes Oct4(A) Ddx4(B) Sycp3(C) after FGSCs are treated with CDPs at different concentrations and time points, where group A has a CDPs concentration of 50 μg/ml, the group B has a CDPs concentration of 5 μg/ml, the group C has a CDPs concentration of 0.5 μg/ml, and the Ctrl group refers to a control group.

Figure 7B:
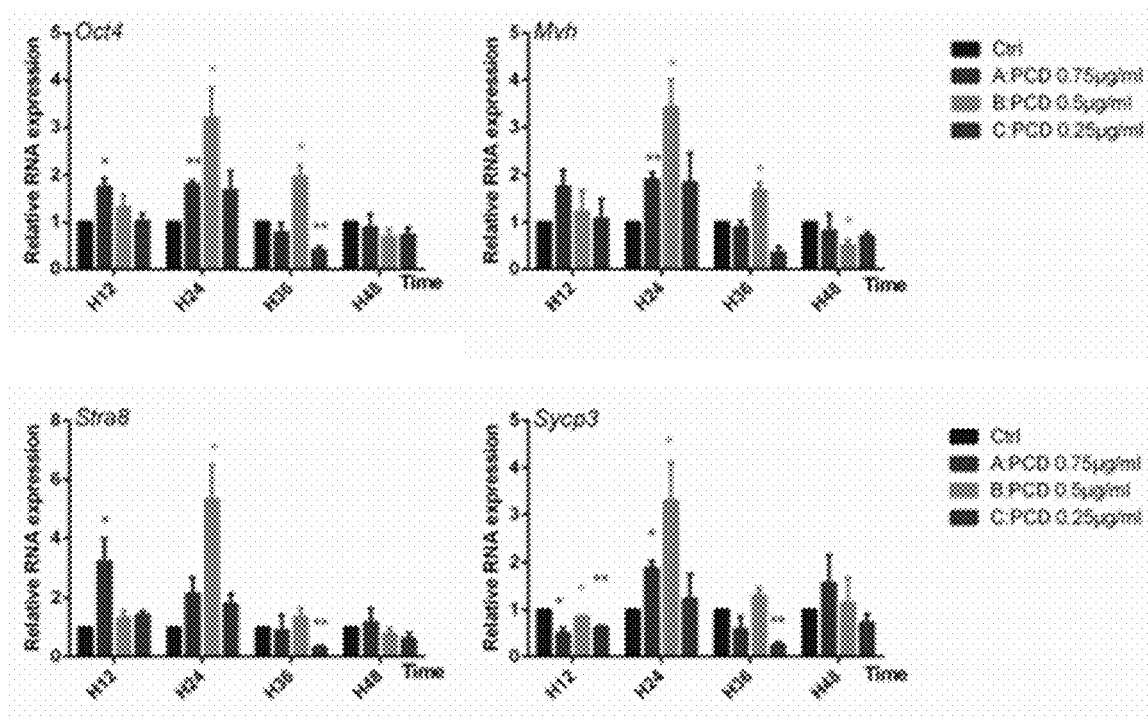
FIG. 7B is a diagram showing the expression of related genes Oct4(A) Ddx4(B) Stra8(C) Sycp3(D) in FGSCs treated with CDPs.

FIG. 7B shows the relative expression of genes Oct4(A) Ddx4(B) Stra8(C) Sycp3(D) after FGSCs are treated with CDPs at different concentrations and time points, where group A has a CDPs concentration of 0.75 μg/ml, group B has a CDPs concentration of 0.5 μg/ml, group C has a CDPs concentration of 0.25 μg/ml, and the Ctrl group refers to a control group.

The data for A, B, and C are expressed as mean±SD of three experiments and processed by ANOVA. * indicates $P<0.05$ and ** indicates $P<0.01$.

9. Detection of the Expression of Related Proteins in Treated FGSCs by IFA
   (1) FGSCs treated with CDPs and normally-cultivated FGSCs are adopted as an experimental group and a control group, respectively. At 12 h, 24 h, 36 h, and 48 h of cultivation, FGSC-growing glass slides in a 24-well plate are immersed in PBS for 3 times, 5 min/time; and the slides are fixed with 4% PFA for 15 min and then immersed in PBS for 3 times, 5 min/time.
   (2) The cells are permeabilized with 0.5% Triton X-100 at room temperature for 10 min, then the Triton is removed, and the slides are immersed in PBS for 3 times, 5 min/time; blocking is conducted for 1 h with BSA at room temperature, without washing; then a rabbit primary antibody Oct4 (diluted at 1:400) and Mvh (diluted at 1:100) are added to the 24-well plate; and the plate is sealed with parafilm and incubated overnight at 4° C.
   (3) The slides are immersed in PBS for 3 times, 5 min/time, a goat anti-rabbit fluorescent secondary antibody (diluted at 1:400) is added in the dark, and the slides are incubated for 1 h in a humidified box at room temperature; and then the slides are immersed in PBS for 3 times, 5 min/time.
   (4) Counter-staining of nuclei: DAPI (diluted at 1:1,000) is dropped, and the slides are incubated in the dark for 3 min (which is determined according to cell quality); excess DAPI is washed away by conducting PBS washing 2 times, 5 min/time; an anti-fluorescence quenching agent is dropped on a glass slide, the stained glass slide is upended on the glass slide, and then the slides are mounted; and observation and image acquisition are conducted under a fluorescence microscope.

Figure 8A:
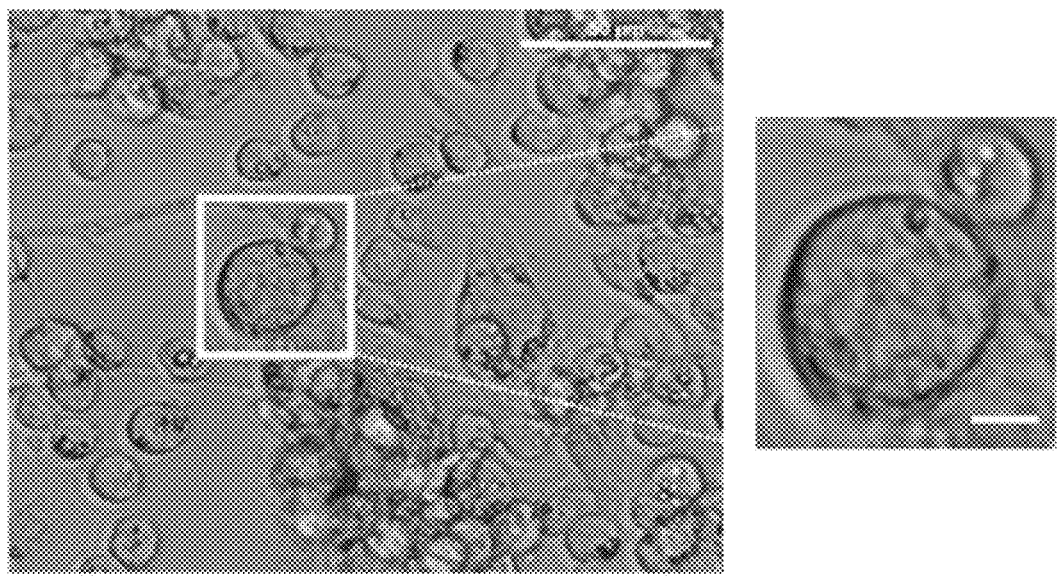
FIG. 8A is a diagram showing the characteristics of differentiation in vitro of mFGSCs at the optimal CDPs concentration of 0.5 µg/ml.
Figure 8B:
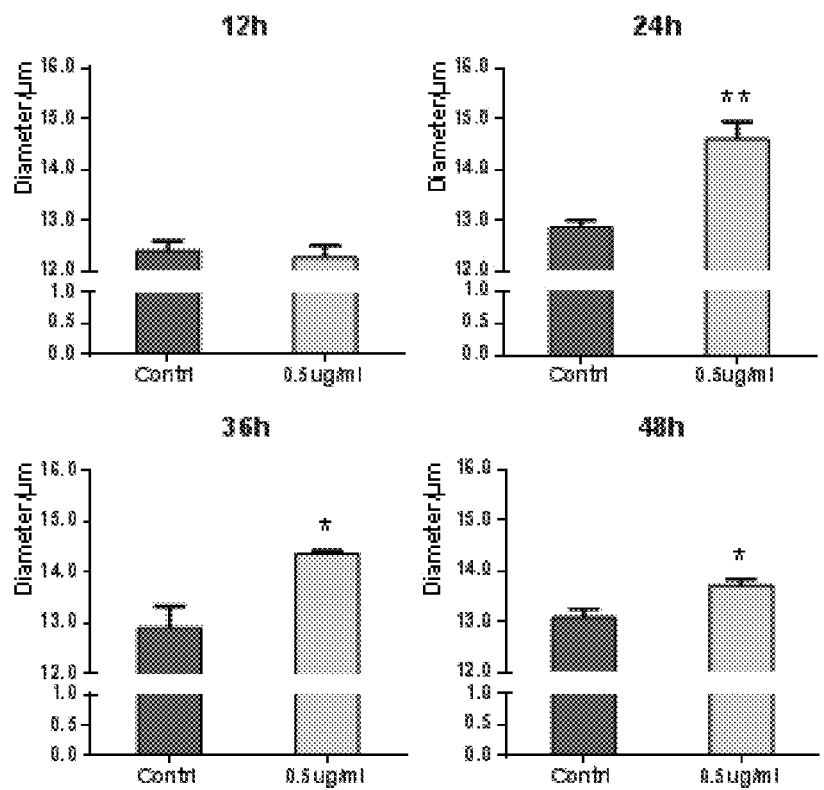
FIG. 8B is a diagram showing the cell diameters in the control group and the experimental group at 12 h, 24 h, 36 h, and 48 h of drug treatment.

The characteristics of differentiation in vitro of mFGSCs at the optimal CDPs concentration of 0.5 μg/ml are shown in FIGS. 8A-B. FIG. 8A shows the representative morphological characteristics of FGSCs at 48 h, with scale lengths of 50 μm and 10 m; and FIG. 8B shows the cell diameters in the control group and the experimental group at 12 h, 24 h, 36 h, and 48 h of drug treatment.

The data are expressed as mean±SEM of four experiments and analyzed by t test. * represents $P<0.05$ and ** represents $P<0.01$.

Figure 9A:
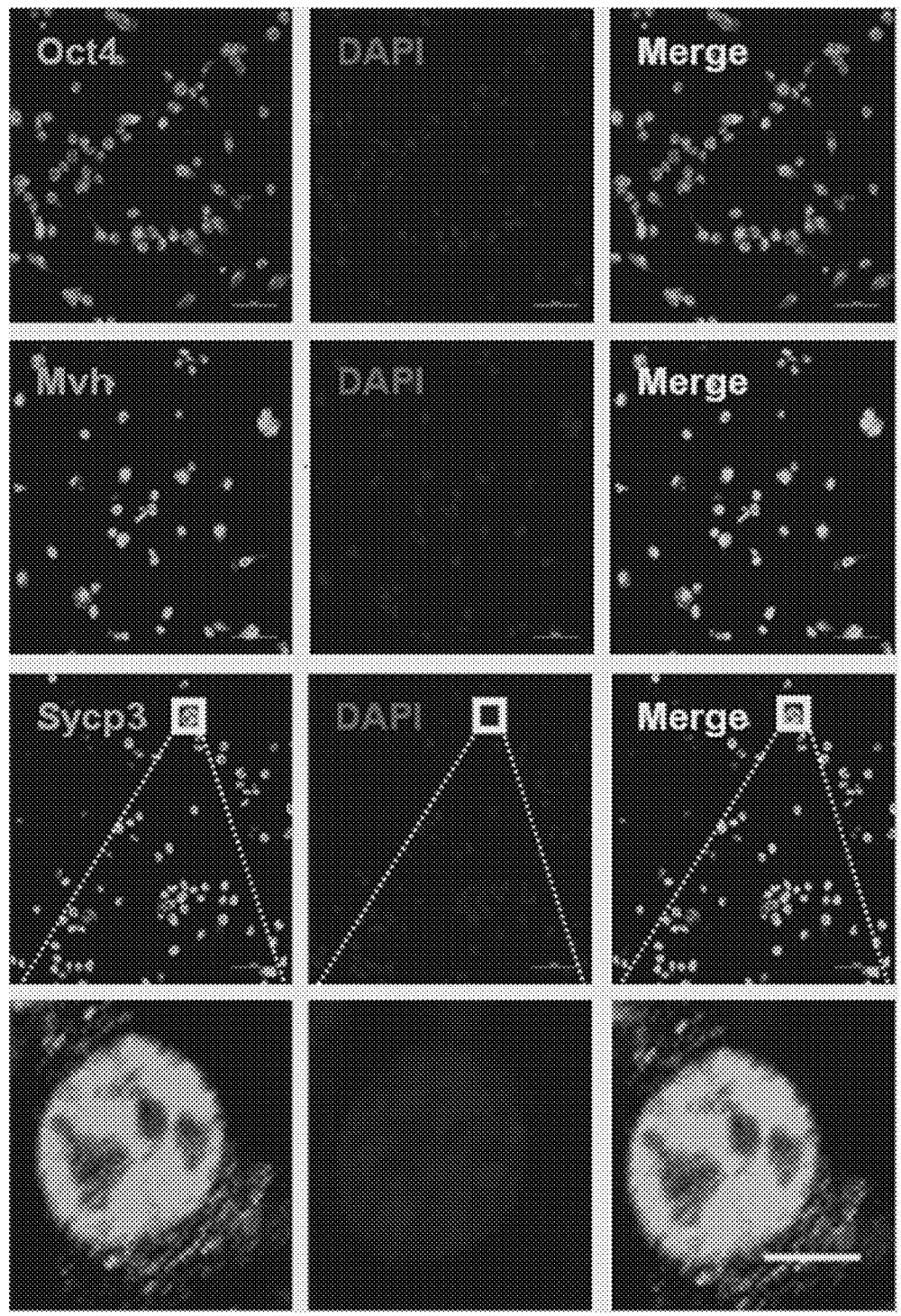
FIG. 9A is a diagram showing the characteristics of mFGSCs cultivated in vitro in the CDPs experimental group.
Figure 9B:
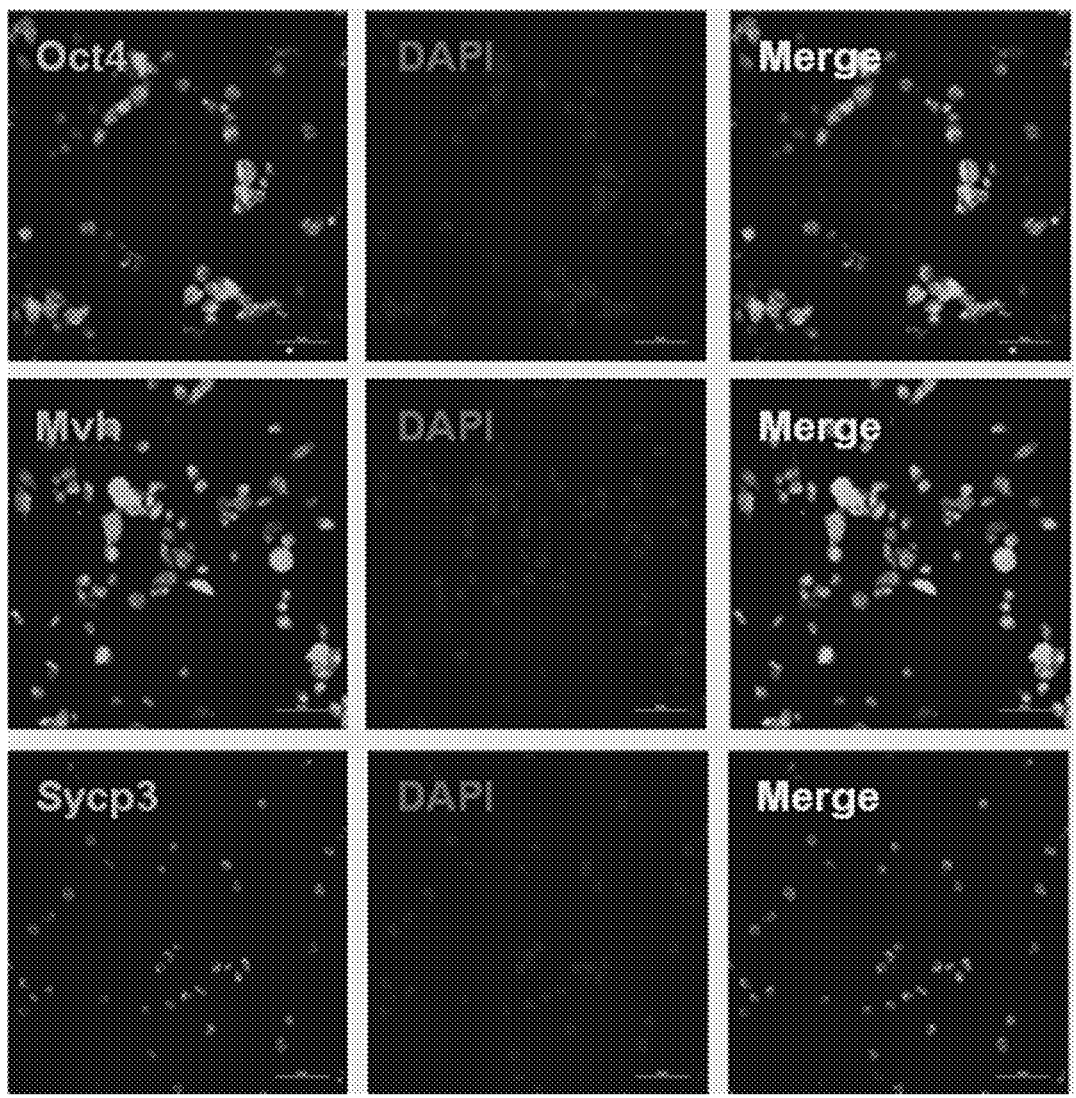
FIG. 9B is a diagram showing the characteristics of mFGSCs cultivated in vitro in the control (Ctrl) group.

The characteristics of mFGSCs cultivated in vitro in the CDPs experimental group and Ctrl group are shown in FIGS. 9A-B. FIG. 9A shows the IFA results of the expression of Oct4, Mvh, and Sycp3 (green) in FGSCs treated with CDPs for 48 h, where, the images are magnified 400 times, with a scale length of 50 μm. FIG. 9B shows the IFA results of the expression of Oct4, Mvh, and Sycp3 (green) in FGSCs of the Ctrl group at 48 h, where, the images are magnified 400 times, with a scale length of 50 μm.

Figure 10:
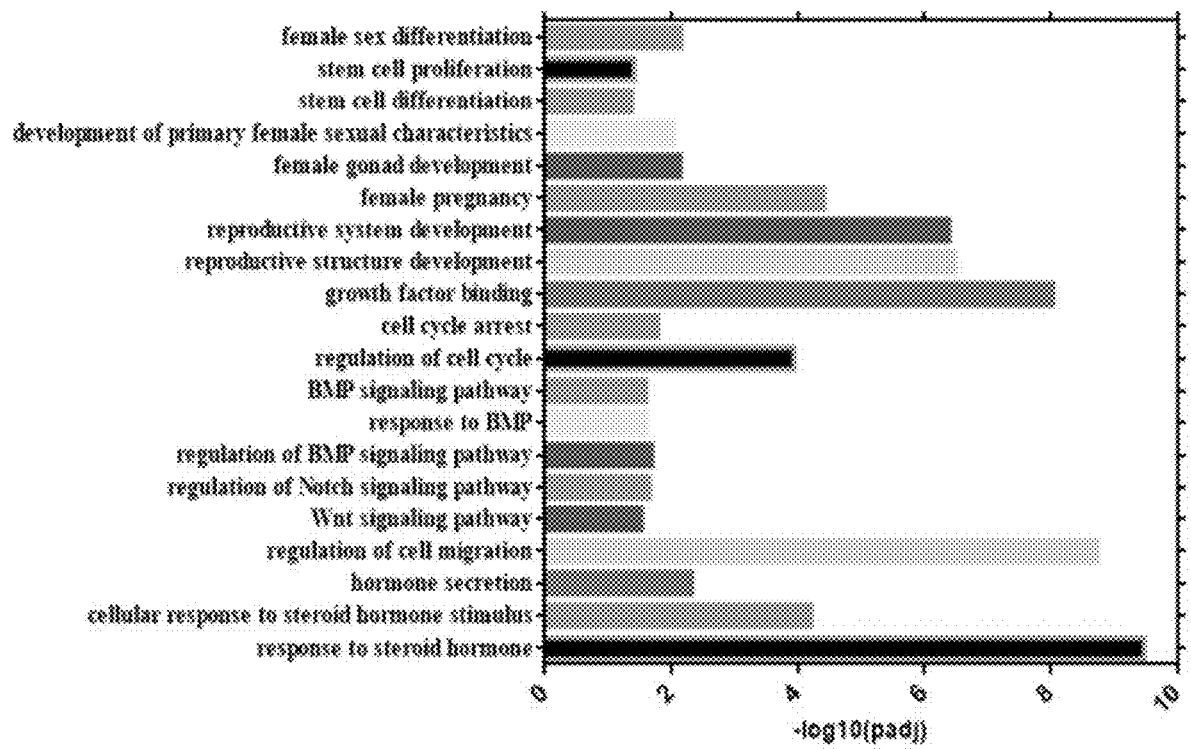
FIG. 10 is a diagram showing the function analysis of differential genes in the mFGSC.vs.mFGSC-CDPs group.
Figure 11:
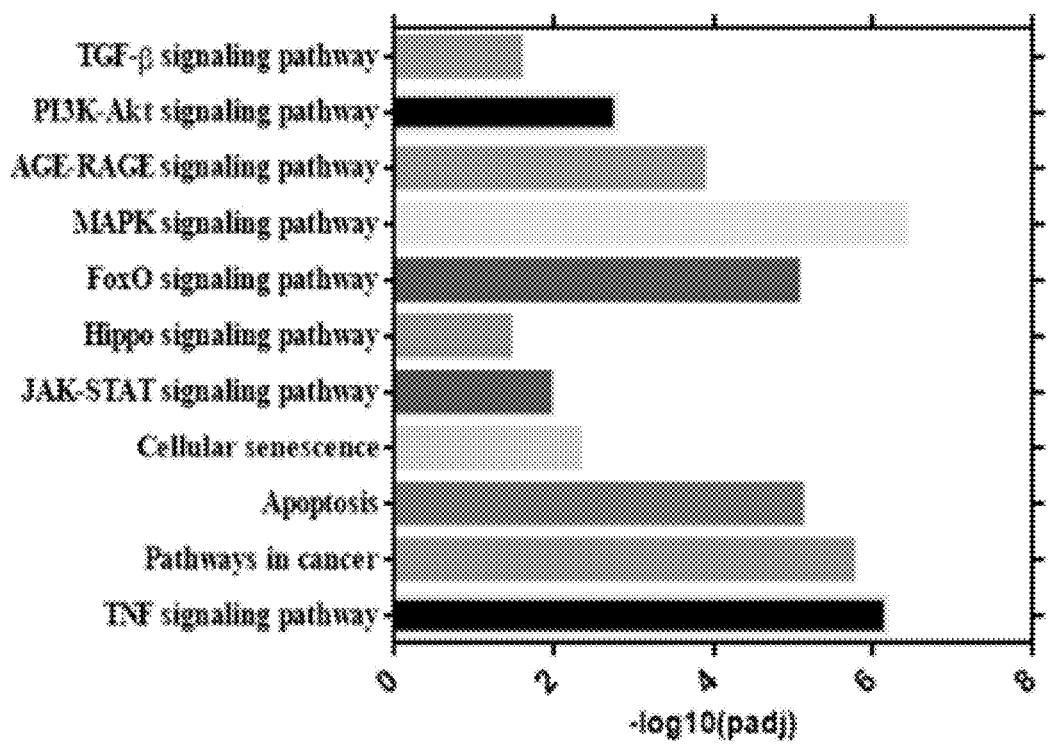
FIG. 11 is a diagram showing the KEGG pathway enrichment analysis of differential genes in the mFGSC.vs.mFGSC-CDPs group.

In the present invention, by sequencing the transcriptome of FGSCs in the control group and the experimental group, it can be known that the differential genes for the mFGSC control group and mFGSC-CDPs experimental group also show different expressions in cell differentiation, cell proliferation, BMP signaling pathway, Nocth signaling pathway, Wnt signaling pathway, cell migration, and so on. Moreover, the stem cells show significant changes in steroid hormone response and growth factor regulation, indicating that the related genes described above play an important role at the developmental stage of mFGSCs, as shown in FIG. 10. Moreover, changes occur to the Hippo signaling pathway, JAK-STAT signaling pathway, and PI3K-Akt signaling pathway that are closely related to germ cell development. Furthermore, there are cytokines related to ovarian germ cell regulation in both the TGF-β family and the TNF family, as shown in FIG. 11.

Figure 12A:
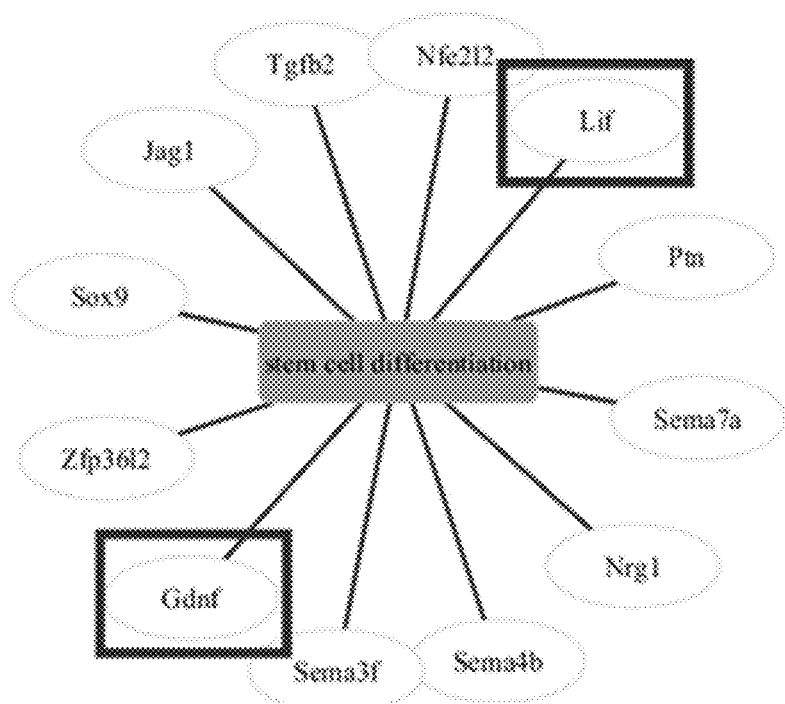
FIG. 12A is a diagram showing differential genes that are down-regulated in the differentiation of stem cells in the mFGSC.vs.mFGSC-CDPs group.
Figure 12B:
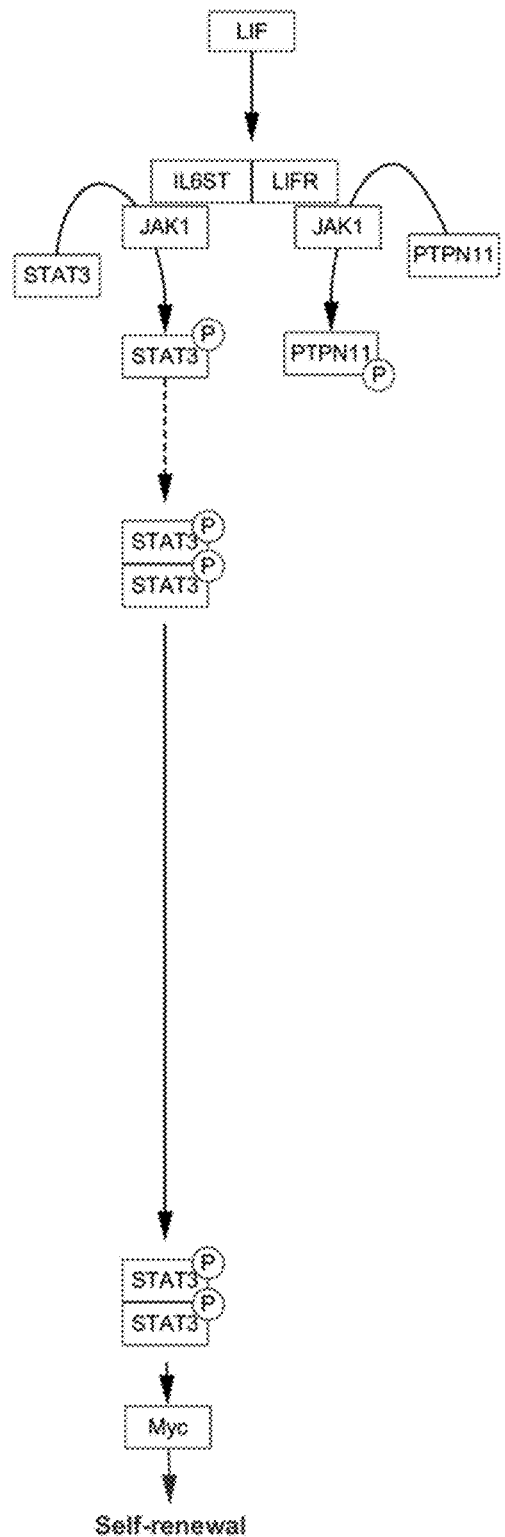
FIG. 12B a diagram showing a signal transduction map of the down-regulated differential gene Lif.
Figure 12C:
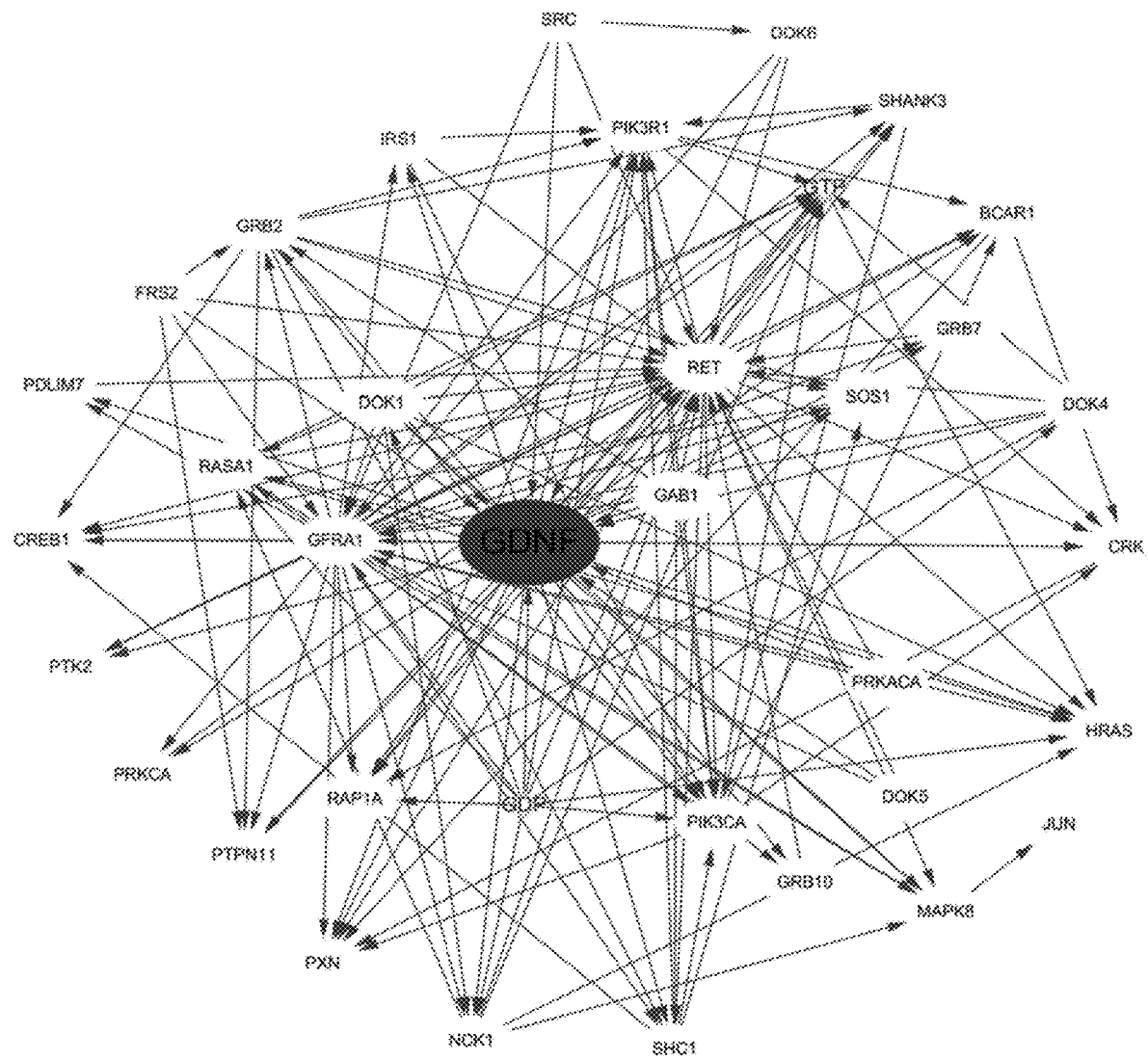
FIG. 12C a diagram showing a signal transduction map of the down-regulated differential gene Gdnf.

Among the differential genes that affect stem cell differentiation, some are down-regulated. As shown in FIG. 12A, two key genes that affect the self-renewal of FGSCs are discovered: Lif (Leukemia inhibitory factor) and Gdnf (Glial cell line-derived neurotrophic factor). In the PI3K/Stat3 signaling pathway, the down-regulation of Lif will weaken the proliferation of stem cells and promote the differentiation of stem cells, as shown in FIG. 12B. Also in the GDNF signaling network, the down-regulation of Gdnf will deplete the microenvironment of GSCs and increase the number of differentiated germ cells, as shown in FIG. 12C.

The results in the above experiment process all are analyzed by the statistical software SPSS 21.0, and measurement data are expressed as mean±SD ($\bar{x}$±s). ANOVA or t test is used to conduct analysis and comparison among the groups. P<0.05 indicates that the difference is statistically significant.

Conclusion:

Through the isolation, purification, and cultivation of FGSCs, cells with stable growth and excellent proliferation activity can be obtained, which will be used as seed cells for subsequent CDPs treatment. RT-PCR and PCR can be used to detect the pluripotency and germline marker gene Oct4, germ cell germline marker genes Mvh Fragilis Dazl, and stem cell pluripotency marker genes Stella/Blimp1/Sycp3 of GSCs, with Gapdh as an internal reference gene, and the cells show corresponding positive expressions of all the genes, indicating that the cells have stable reproducibility and pluripotency. EdU IFA results show that FGSCs have positive expression, indicating that the cells have high proliferation activity. After FGSCs are treated with CDPs at different concentrations, the cell proliferation is assayed by the CCK8 method, and results show that 0.5 μg/ml among the first CDPs screening concentrations is the optimal concentration. The experimental group at the optimal concentration has a cell proliferation activity close to that of the control group, but the experimental groups at the concentrations of 50 μg/ml and 5 μg/ml both have a proliferation activity lower than that of the control group. QF-PCR detection results of related genes show that the GSC pluripotency and germline marker gene Oct4 and the germline reproductive marker gene Mvh are significantly increased at 12 h and 36 h of CDPs treatment, and the stem cell pluripotency marker Sycp3 is significantly increased at 12 h and 36 h of CDPs treatment; and according to a comprehensive comparison, the 0.5 μg/ml group shows the most significant effect, with statistically-significant difference.

After the preliminary screening of CDPs concentrations, the following CDPs at second screening concentrations are set based on the optimal concentration of 0.5 μg/ml for further treating FGSCs: 0.75 μg/ml, 0.5 μg/ml, and 0.25 μg/ml. The cell proliferation activity results of the experimental groups detected by the CCK8 method are all different from that of the control group, but the difference is relatively little, which is consistent with the above experimental results. The QF-PCR results show that the GSC pluripotency and germline marker gene Oct4 and the germline reproductive marker gene Mvh are significantly increased at 24 h of CDPs treatment, and the stem cell pluripotency markers Stra8 and Sycp3 are significantly increased at 24 h of CDPs treatment; and according to a comprehensive comparison, the 0.5 μg/ml group still shows the most significant effect, with statistically-significant difference. According to the above experiment, the optimal concentration of CDPs for treating FGSC is 0.5 μg/ml, so the cells are further cultivated at this concentration, and differentiated FGSCs are obtained at 48 h of treatment. A morphology diagram of the cells cultivated in vitro shows the diameter and morphological changes of FGSCs. IFA results show that the stem cells have positive expression of the pluripotency marker protein Sycp3. In conclusion, the research results show that CDPs can significantly induce the differentiation of FGSCs at a concentration of 0.5 μg/ml. Cell RNA-sequence analysis shows that the signaling pathways related to mFGSC proliferation and differentiation are significantly different from the functions of differential genes for stem cell growth and development. In the proliferation and differentiation of stem cells, the down-regulation of key genes Lif and Gdnfindicates the reduction of cell self-renewal ability and the increase of differentiation ability. The influence of CDPs on cells is of significance for the construction of an in vitro induced differentiation system for FGSCs.

What is claimed is:

1. A method of obtaining oocytes from female germline stem cells (FGSCs) comprising: culturing FGSCs in a media comprising *Cistanche deserticola* polysaccharides (CDPs) to obtain oocytes.

2. The method according to claim 1, wherein the medium comprises: an α-minimum essential medium (α-MEM), 1 mM non-essential amino acids (NEAAs), 2 mM L-glutamine, 1 mM sodium pyruvate, 0.1 mM β-mercaptoethanol (β-ME), 10 ng/mL leukemia inhibitory factor (LIF), 10 ng/mL epidermal growth factor (EGF), 40 ng/mL glial cell line-derived neurotrophic factor (GDNF), 1 ng/mL basic fibroblast growth factor (bFGF), 10% fetal bovine serum (FBS), and 15 mg/mL penicillin/streptomycin.

3. The method according to claim 1, wherein the CDPs are added to the medium at an amount of 0.25 μg/mL to 0.75 μg/mL, and then the FGSCs are cultivated.

4. The method according to claim 3, wherein the FGSCs are cultivated for 12 h to 48 h.

5. The method according to claim 4, wherein the CDPs are added at an amount of 0.5 μg/mL and the FGSCs are cultivated for 24 h to 48 h.

6. The method according to claim 2, wherein the CDPs are added to the medium at an amount of 0.25 μg/mL to 0.75 μg/mL, and then the FGSCs are cultivated.

* * * * *